US008911396B2

(12) United States Patent
Gordon (10) Patent No.: US 8,911,396 B2
(45) Date of Patent: Dec. 16, 2014

(54) SHEATH

(75) Inventor: Gregory Gordon, Omaha, NE (US)

(73) Assignee: Board Of Regents Of The University Of Nebraska, Lincoln, NE (US)

(*) Notice: Subject to any disclaimer, the term of this patent is extended or adjusted under 35 U.S.C. 154(b) by 0 days.

(21) Appl. No.: 13/516,290

(22) PCT Filed: Dec. 15, 2010

(86) PCT No.: PCT/US2010/060556
§ 371 (c)(1),
(2), (4) Date: Sep. 12, 2012

(87) PCT Pub. No.: WO2011/084505
PCT Pub. Date: Jul. 14, 2011

(65) Prior Publication Data
US 2013/0006163 A1 Jan. 3, 2013

Related U.S. Application Data

(60) Provisional application No. 61/286,408, filed on Dec. 15, 2009.

(51) Int. Cl.
*A61M 25/00* (2006.01)
(Continued)

(52) U.S. Cl.
CPC ....... *A61M 25/0662* (2013.01); *A61M 25/0097* (2013.01); *A61B 17/3478* (2013.01);
(Continued)

(58) Field of Classification Search
CPC ............. A61M 25/0102; A61M 25/0169; A61M 25/0172; A61M 25/0194; A61M 25/02; A61M 25/0606; A61M 25/0662; A61M 25/01; A61M 39/08; A61M 39/10; A61M 2025/028; A61M 2039/0009; A61M 29/00; A61M 2025/0681; A61M 25/0097; A61M 2025/003; A61M 2025/0031; A61M 2039/1077; A61M 39/06; A61M 2039/06; A61M 2039/062; A61M 2039/0686; A61B 17/32056; A61B 17/3207; A61B 17/3205; A61B 17/3415; A61B 17/3496; A61B 2017/00238; A61B 2017/3205; A61B 2017/3207; A61B 2017/3209; A61B 2017/3441; A61B 17/34; A61B 17/3462; A61B 17/3478; A61B 17/3498; A61B 2017/3417; A61B 2017/3419; A61B 2017/3423
USPC ............... 604/8, 9, 10, 4.01, 5.01, 5.02, 6.05, 604/6.06, 6.15, 6.16, 174, 175, 177, 178, 604/179, 180, 48, 93.01, 164.01, 164.02, 604/164.03, 164.04, 164.06, 164.07, 604/164.08, 164.09, 164.1, 164.11
See application file for complete search history.

(56) References Cited

U.S. PATENT DOCUMENTS 3,853,126 A 12/1974 Schulte
3,998,222 A 12/1976 Shihata
(Continued)

OTHER PUBLICATIONS

International Preliminary Report on Patentability in International Application No. PCT/US2010/060556, issued Jun. 19, 2012, 4 pages.

(Continued)

*Primary Examiner* — Adam Marcetich
(74) *Attorney, Agent, or Firm* — Fish & Richardson P.C.

(57) ABSTRACT

The present application includes a sheath that is suitable for use in a variety of medical procedures. In one or more implementations, the sheath includes a shunt member, and a curvable portion. The curvable portion may be configured in various orientations to facilitate an intervention, such as a hemodialysis intervention, or the like, by an operator. The curvable portion may be configured to bend between a substantially straight configuration and a curved configuration. In implementations, the sheath may be configured to have detachable and/or interchangeable components (e.g., shunt member, curvable portion, etc.).

16 Claims, 9 Drawing Sheets

(51) Int. Cl.
*A61M 39/00* (2006.01)
*A61M 37/00* (2006.01)
*A61M 25/06* (2006.01)
*A61B 17/34* (2006.01)
*A61M 25/01* (2006.01)
*A61M 39/08* (2006.01)
*A61M 25/02* (2006.01)

(52) U.S. Cl.
COC ....... *A61M 2025/0681* (2013.01); *A61B 17/34* (2013.01); *A61B 2017/3419* (2013.01); *A61B 17/3462* (2013.01); *A61B 17/3498* (2013.01); *A61M 25/01* (2013.01); *A61M 25/02* (2013.01); *A61M 39/08* (2013.01); *A61M 2025/028* (2013.01); *A61M 2039/0009* (2013.01)
USPC .............. 604/93.01; 604/164.01; 604/164.02; 604/164.07; 604/164.08; 604/164.09

(56) References Cited

U.S. PATENT DOCUMENTS

| | | | |
|---|---|---|---|
| 4,316,461 A * | 2/1982 | Marais et al. | 604/179 |
| 4,453,933 A * | 6/1984 | Speaker | 604/179 |
| 4,840,613 A * | 6/1989 | Balbierz | 604/533 |
| 4,850,954 A | 7/1989 | Charvin | |
| 4,865,586 A | 9/1989 | Hedberg | |
| 4,976,698 A * | 12/1990 | Stokley | 604/174 |
| 5,031,775 A * | 7/1991 | Kane | 206/571 |
| 5,443,460 A * | 8/1995 | Miklusek | 604/530 |
| 5,538,513 A * | 7/1996 | Okajima | 604/527 |
| 5,647,859 A * | 7/1997 | Lampropoulos et al. | 604/264 |
| 5,902,274 A * | 5/1999 | Yamamoto et al. | 604/164.12 |
| 5,916,199 A * | 6/1999 | Miles | 604/174 |
| 5,947,931 A * | 9/1999 | Bierman | 604/180 |
| 5,989,223 A * | 11/1999 | Chu et al. | 604/167.05 |
| 6,001,081 A * | 12/1999 | Collen | 604/174 |
| 6,113,577 A * | 9/2000 | Hakky et al. | 604/174 |
| 7,198,066 B2 * | 4/2007 | Kagenow | 138/110 |
| 7,553,326 B2 | 6/2009 | Sweet | |
| 2001/0053895 A1 * | 12/2001 | Vaillancourt | 604/243 |
| 2002/0087108 A1 * | 7/2002 | Maginot et al. | 604/5.04 |
| 2002/0107479 A1 * | 8/2002 | Bates et al. | 604/96.01 |
| 2004/0087905 A1 * | 5/2004 | Breznock et al. | 604/164.04 |
| 2004/0153021 A1 * | 8/2004 | Osborne et al. | 604/1 |
| 2005/0113799 A1 * | 5/2005 | Lenker | 604/509 |
| 2005/0165364 A1 | 7/2005 | DiMatteo | |
| 2005/0209584 A1 * | 9/2005 | Rome | 604/536 |
| 2005/0234405 A1 * | 10/2005 | Dikeman et al. | 604/180 |
| 2006/0009737 A1 * | 1/2006 | Whiting et al. | 604/135 |
| 2006/0047266 A1 * | 3/2006 | Elkins et al. | 604/528 |
| 2006/0074398 A1 * | 4/2006 | Whiting et al. | 604/510 |
| 2006/0084927 A1 * | 4/2006 | Formichi | 604/272 |
| 2006/0129091 A1 * | 6/2006 | Bonnette et al. | 604/93.01 |
| 2006/0129112 A1 * | 6/2006 | Lynn | 604/256 |
| 2006/0129134 A1 * | 6/2006 | Kerr | 604/539 |
| 2007/0161956 A1 * | 7/2007 | Heuser | 604/164.1 |
| 2007/0167901 A1 * | 7/2007 | Herrig et al. | 604/6.16 |
| 2007/0225680 A1 * | 9/2007 | Biggins | 604/526 |
| 2008/0171944 A1 | 7/2008 | Brenneman | |
| 2008/0195046 A1 * | 8/2008 | Altman | 604/117 |
| 2009/0306574 A1 | 12/2009 | Kopperschmidt | |
| 2010/0030162 A1 * | 2/2010 | Cremascoli et al. | 604/246 |
| 2012/0130151 A1 * | 5/2012 | Kassab et al. | 600/16 |

OTHER PUBLICATIONS

International Search Report and Written Opinion in International Application No. PCT/US2010/060556, mailed Aug. 31, 2011, 6 pages.
Supplementary European Search Report in EP Application 10842550.5, dated Nov. 29, 2013, 7 pages.

* cited by examiner

SHEATH

BACKGROUND

Sheaths are employed in a wide variety of medical procedures. For example, sheaths may be utilized when performing vascular procedures, genitourinary track procedures, gastrointestinal tract procedures, and the like. For example, individuals with renal failure require some form of hemofiltration in order to survive. The vast majority of these patients survive through hemodialysis. Most of these patients receive their hemodialysis through permanent, high flow, vascular conduits, created surgically in their extremities. Over time, these conduits can stop functioning adequately. One of the key elements of survival in this patient population is maintenance of adequate vascular access and function of these vascular conduits. In order to achieve this, the conduits require repair and maintenance throughout their lifespan. These repairs are usually performed in an interventional radiology suite, cardiology suite, and/or operating room by percutaneous (access from skin to conduit without large incision) technique. Sheaths are minimally invasive interventional tools used in such techniques.

Sheaths comprise temporary, external, conduit extensions that facilitate repair of the internal, permanent conduit from the inside. These conduit extensions communicate most commonly through the vascular system, but also can act as conduits between the external environment and any internal plumbing system, e.g. arterial, venous, biliary, portal venous, gastrointestinal tract, renal collecting system, excluded aortic aneurysm sac, central canal/thecal sac/epidural space. In this way, large incisions are avoided, recovery is quicker, treatment is less expensive versus surgery, and the life span of the veins and arteries used is prolonged. Generally, one to two sheaths are employed during each intervention.

SUMMARY

A sheath is described that is suitable for use in a variety of medical procedures. In one or more implementations, the sheath includes a shunt member, and a curvable portion. The curvable portion may be configured in various orientations to facilitate an intervention, such as a hemodialysis intervention, or the like, by an operator. The curvable portion may be configured to bend between a substantially straight configuration and a curved configuration. In implementations, the sheath may be configured to have detachable and/or interchangeable components (e.g., shunt member, curvable portion, etc.).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference numbers in different instances in the description and the figures may indicate similar or identical items.

DETAILED DESCRIPTION

Overview

Existing sheaths are straight or have internal curves (i.e., curves within the patient). Internal curves aid in the effectiveness for certain procedures in the vascular system, but have no significant function in dialysis intervention/repair. Although effective in their purpose, existing sheaths are hampered by limitations.

One limitation is due to the shape, flow, and direction of the permanent vascular conduit, such as an arterial-venous fistula (AVF) or arterial-venous graft (AVG). The direction of flow is from the artery to the vein, either directly or through a graft. The arterial limb of the AVF travels from proximal to distal, while the venous limb travels from distal to proximal. Therefore, access through these sheaths may occur from two separate and opposite directions, which may produce technical difficulties due to the fact that the primary operator cannot be positioned in two polar opposite directions at the same time. Treatment from one direction also can be hindered by the proximity of the sheath in relation to the rest of the patient's body impeding the ease of work.

In addition, in order to repair AVFs via percutaneous or other minimally invasive techniques, angiography machines are required. Angiography machines utilize medical imaging techniques such as radiation to visualize the blood vessels and conduits of the patient. Radiation exposure is a concern to operators, who often perform multiple procedures in a given day. Moreover, interventional, minimally invasive repair of vascular, genitourinary tract, gastrointestinal tract, biliary, portal venous, musculoskeletal and central nervous system procedures may also expose the operator and patient to increased radiation exposure depending on technical difficulties of location of percutaneous/minimally invasive access of the conduit system of the patient in relation to the angiography machine.

In one implementation, the present disclosure allows for improved hemodialysis access intervention, which allows for dialysis access intervention of both sides (limbs) of the dialysis conduit from the same operator position. Furthermore, the present disclosure may allow an operator, as well as the patient, to receive lower radiation exposure as well as decrease the total time of the intervention procedure.

Therefore, a sheath with an external curvable portion is disclosed. The sheath allows for dialysis access intervention of both sides (limbs) of a dialysis conduit from the same operator position. In one or more implementations, a sheath includes a detachable shunt member, and a detachable curvable portion. The curvable portion is configured to bend between a substantially straight configuration and a curved configuration to facilitate hemodialysis intervention by an operator. In an implementation, the curvable portion may retain a 180° curve when the curvable portion is positioned in the curved configuration. In the curved configuration, the curvable portion may be held in position via a clasp. The clasp is configured to hold the curvable portion in the curved configuration. In an implementation, the clasp is coupled to at least one of a first end of the curvable portion or the second end of the curvable portion. Moreover, the clasp may be selectively coupled at a position proximate to the other of the first end of the curvable portion and the second end of the curvable portion. In yet another implementation, the curvable portion may comprise a semi-rigid material. In this implementation, the curvable portion retains its curved configuration once the operator/technician has positioned the sheath in the desired curved configuration.

It is also contemplated that the sheath may also be comprised of detachable components. In an implementation, the shunt member may be comprised of a detachable shunt member. For example, access to an excluded aortic aneurysm with an aneurysm leak may require a longer sheath member (e.g., fifteen (15) centimeters). The detachable components may be interchangeable with other detachable components adapted for use in the sheath. Moreover, the exterior curvable portion, in conjunction with the detachable components, allows for improved operator/technician access to the patient.

Example Sheath

Generally referring to FIGS. 1A through 11, an implementation of a sheath 10 configured for hemodialysis access and intervention is illustrated. A detachable shunt member 12 may be provided with a dilator 14. The detachable shunt member 12 is configured to extend through a perforation in a side wall, or a superficial wall, of an internal patient conduit source (e.g., a blood vessel) and into an anatomical conduit (e.g., the blood vessel) of a patient. The detachable shunt member 12 may vary in length depending on the use of shunt member 12. For example, the shunt 12 may be about five (5) centimeters in length. The shunt 12 is coupled with a curvable portion 16 by a member 18. In an implementation, member 18 may be configured as a detachable member 18. Detachable member 18 may include a septum (not shown) that is configured to receive other medical devices (i.e., needles, wire, etc.) if detachable curvable portion 16 is not required. In a further implementation, member 18 may be manufactured as a unitary member with shunt 12. In the unitary configuration, member 18 may include a notch 34 adapted to receive clasp 30. In an implementation, detachable curvable portion 16 may be flexible and is capable of forming a "tennis racket" shape. In another implementation, as illustrated in FIG. 1B, curvable portion 16 may be bendable and semi-rigid to allow the curvable portion 16 to retain its curved configuration once an operator/technician has positioned the sheath 10 in the desired curved configuration. The sheath 10 may be configured to be curvable or bendable between 0° and 180°. The curvable portion 16 may be implemented as a tube, or the like. Curvable portion 16 may form an arc having a diameter of about two (2) centimeters to about four (4) centimeters. In a specific implementation, the curvable portion 16 may form an arc having a diameter of about three (3) centimeters. In example implementations, the sheaths 10 may be about five (5) to about eight (8) French in external diameter. However, the overall length of sheath 10, the dimensions of the external curve of detachable curvable portion 16, the degree of curve of detachable curvable portion 16, and the length of internal (i.e., shunt 12, etc.) and external (curvable portion 16, etc.) portions of sheath 10 can vary specific to type and location of the intervention.

Figure 1A:
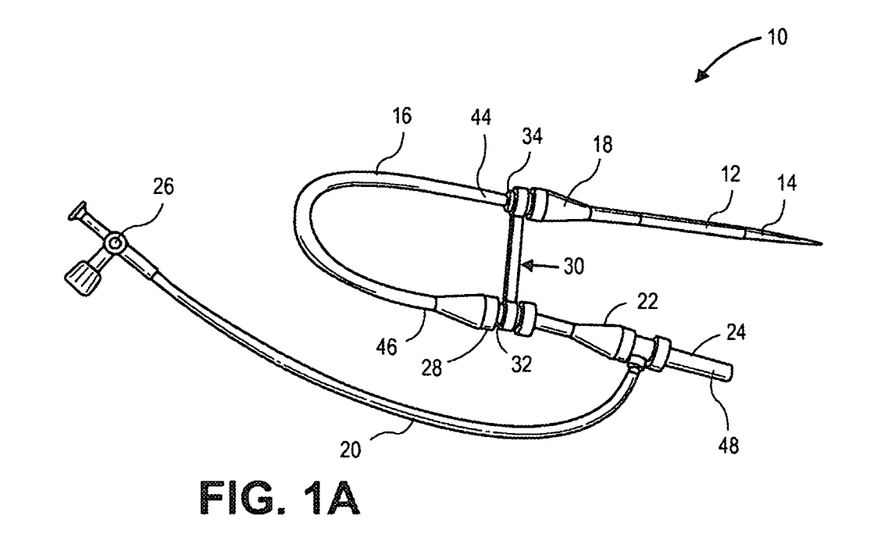
FIG. 1A is a diagrammatic isometric view illustrating an example sheath in accordance with the present disclosure.
Figure 1B:
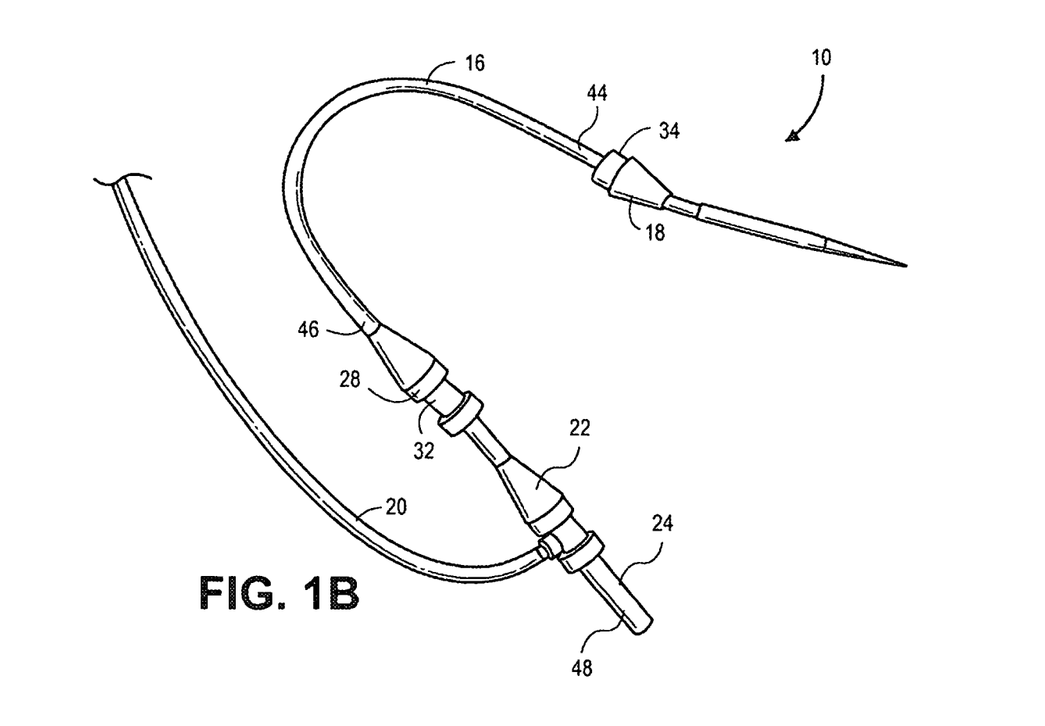
FIG. 1B is a diagrammatic isometric view illustrating another implementation of example sheath in accordance with the present disclosure, wherein the detachable curvable portion is comprised of a semi-rigid material configured to retain the desired curved configuration.
Figure 2:
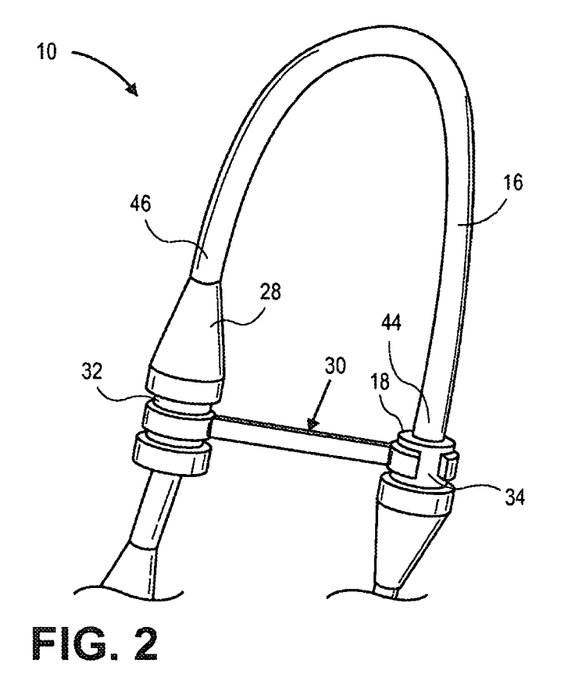
FIG. 2 is a diagrammatic isometric view illustrating the sheath depicted in FIG. 1A, where the sheath is in a closed position.
Figure 5:
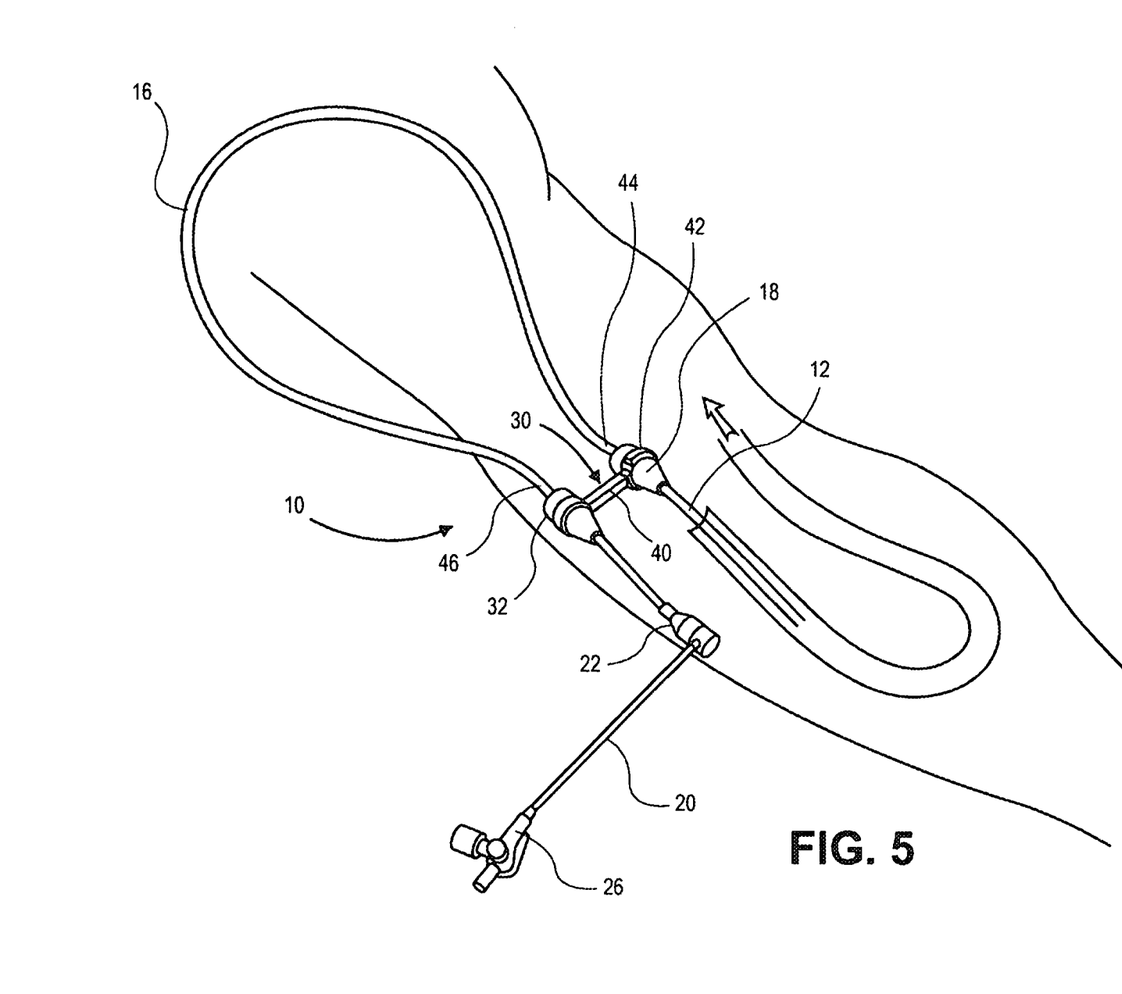
FIG. 5 is a diagrammatic, environmental isometric view illustrating the sheath in FIG. 1A, where a shunt member is inserted into an anatomical conduit of a patient's arm.
Figure 6:
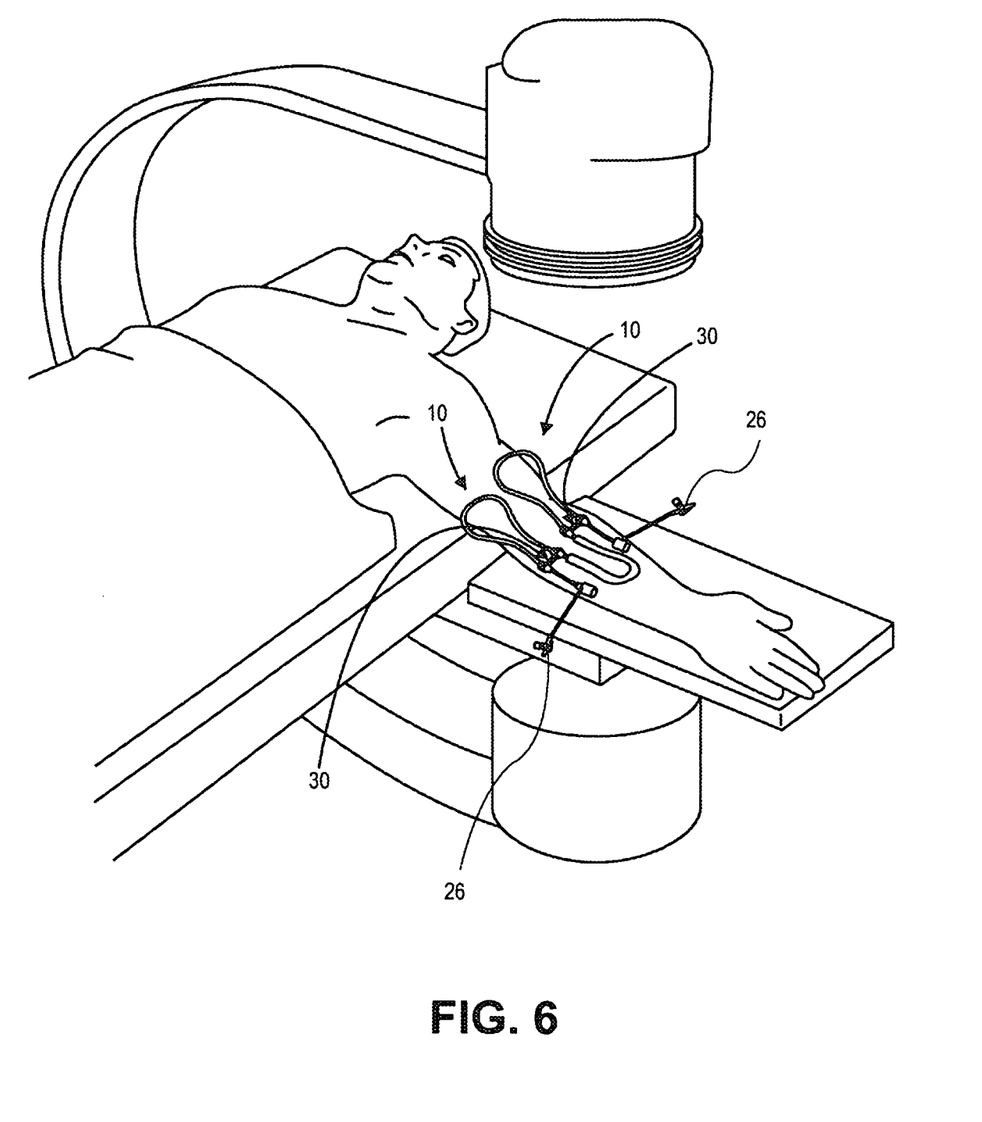
FIG. 6 is a diagrammatic, environmental isometric view illustrating two sheaths in accordance with the present disclosure, where both sheaths are inserted into one or more anatomical conduit(s) of a patient's arm.
Figure 7:
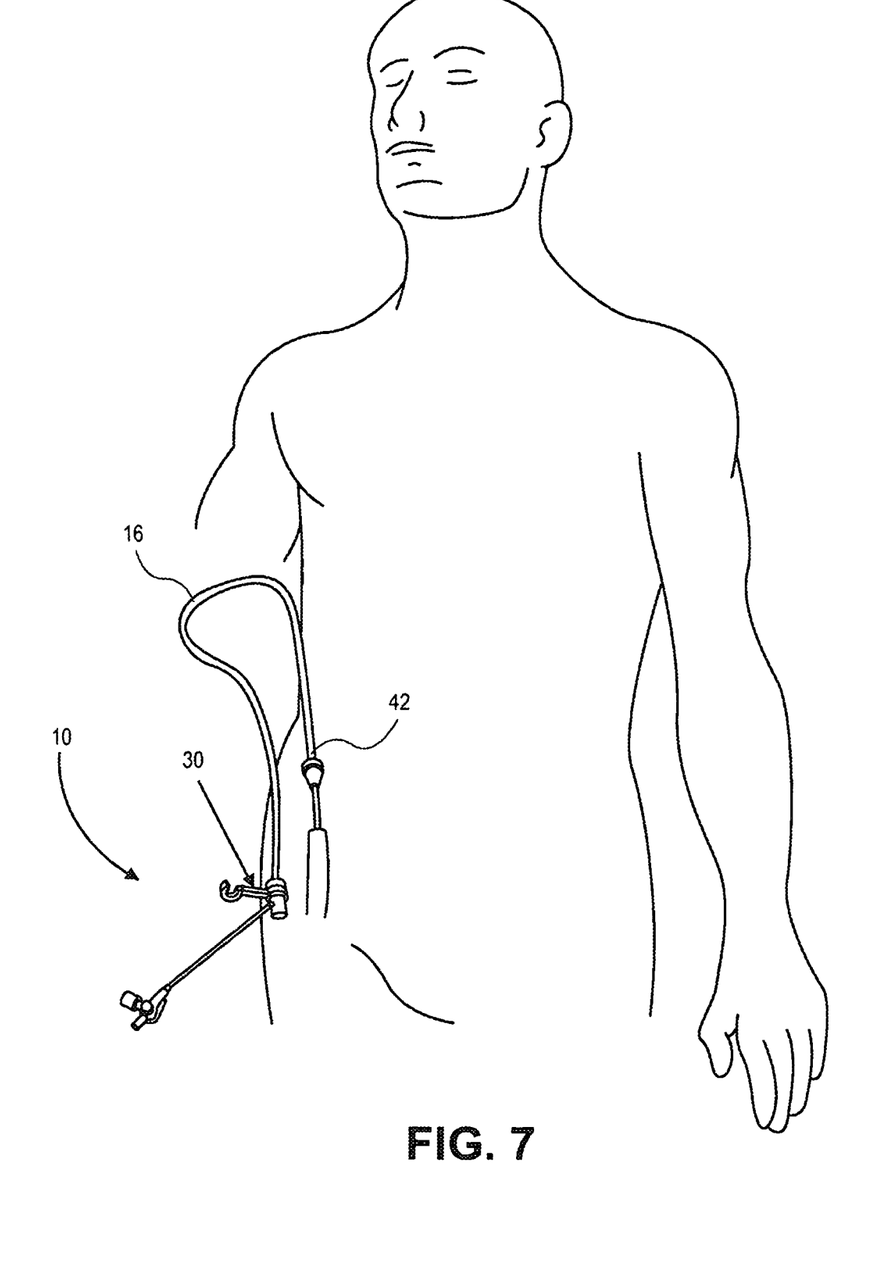
FIG. 7 is another diagrammatic, environmental isometric view illustrating the sheath as illustrated in FIG. 1A, where the sheath is inserted into an anatomical conduit of a patient.
Figure 8:
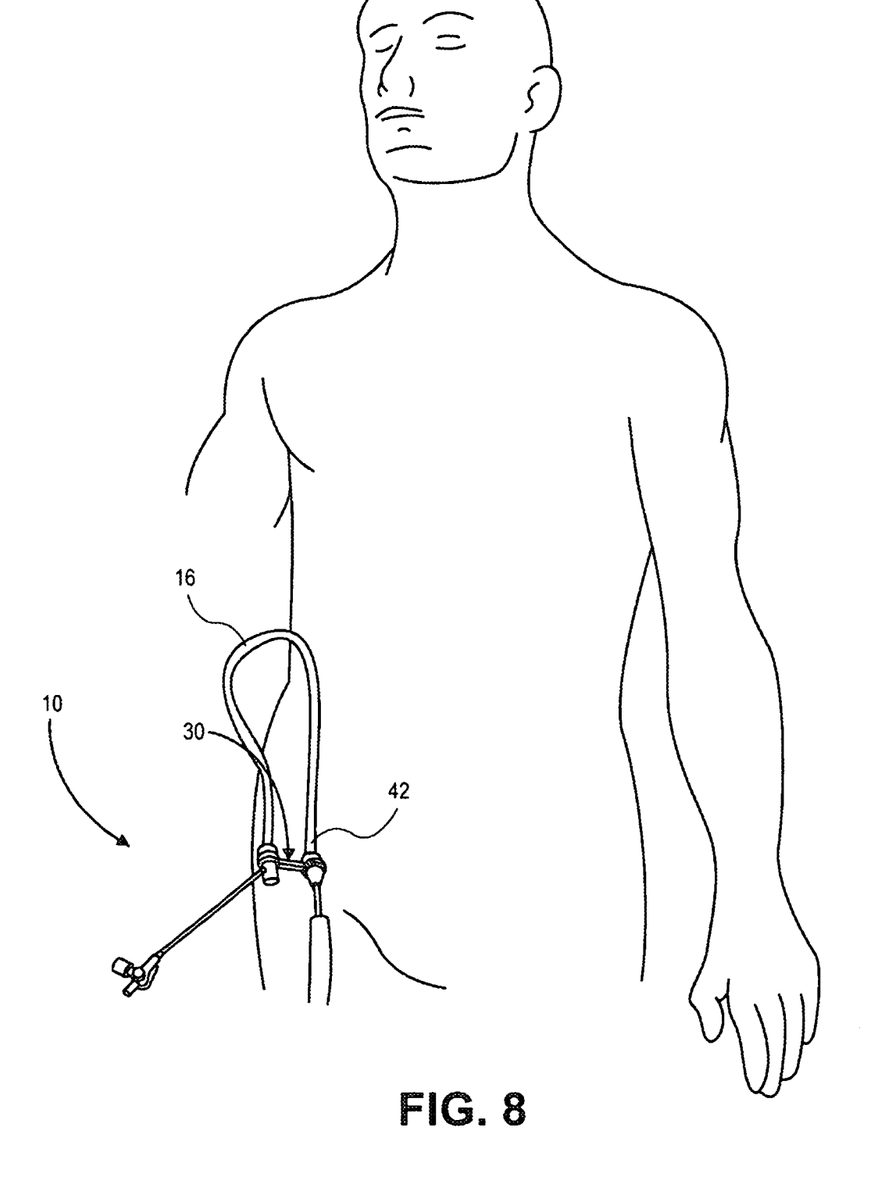
FIG. 8 is another diagrammatic, environmental isometric view illustrating the sheath as illustrated in FIG. 1A, where the sheath is inserted into an anatomical conduit of a patient.
Figure 9:
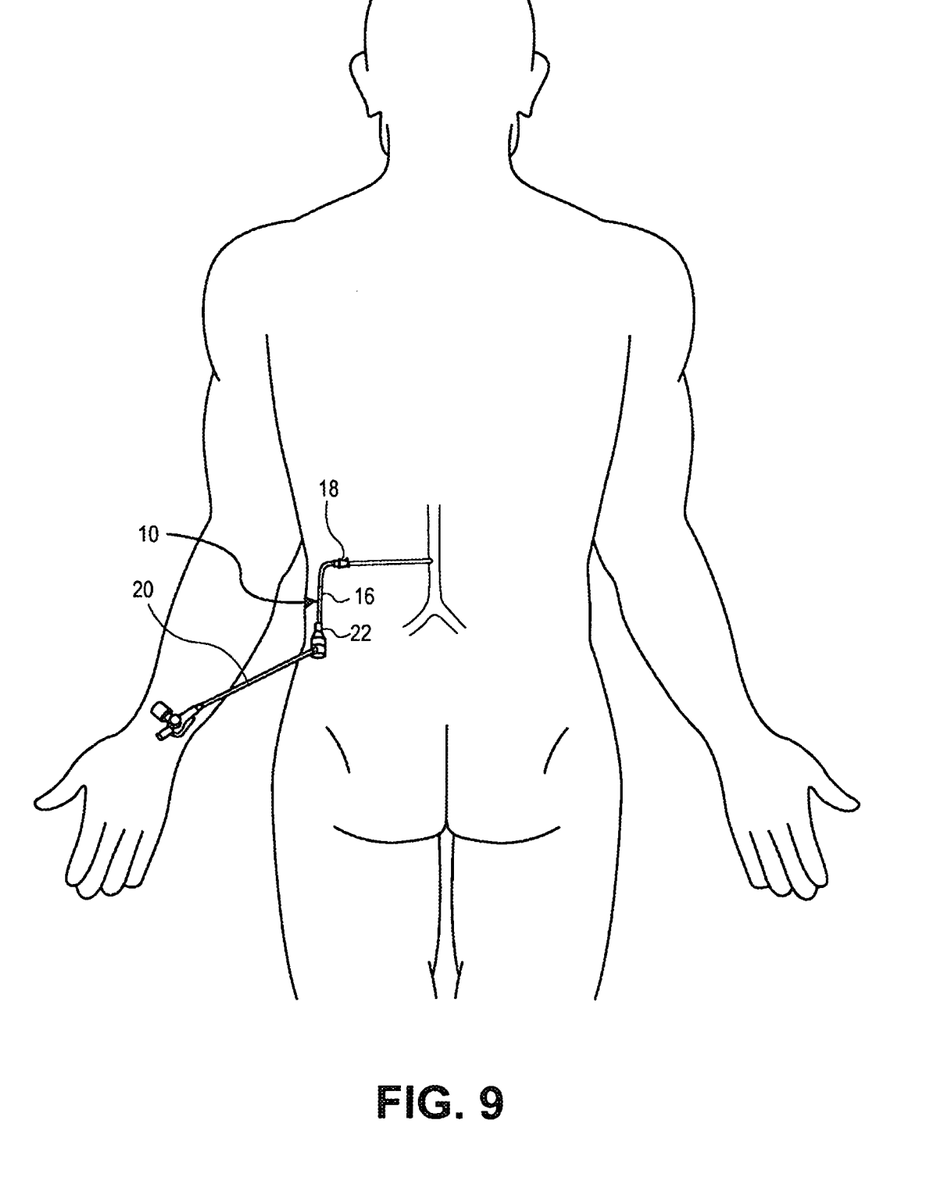
FIG. 9 is a diagrammatic, environmental isometric view illustrating another implementation of a sheath, where the curvable portion is in a substantially straight configuration and the sheath is inserted into an anatomical conduit proximate to a patient's back side.

A tube 20 may be attached to a septum hub 22 having an introducer dilator 24 and a detachable 3-way, large bore, stop cock 26. In an implementation, the lumen (not shown) of the exposed end of the screwable tubing 20 is comparable in size to the respective lumen of a large bore dialysis sheath. Tube 20 is utilized for injection of contrast, fluids, and medications. Tube 20 may also be utilized to aspirate clot and blood and allow for improved suction/aspiration of the thrombus/clot. In an implementation, the tube 20 is configured to have a forty-five (45) degree angle. However, it is contemplated that the tubing 20 may be implemented in various other configurations (e.g., to have different angles of curvature) without departing from the spirit of the disclosure. Septum hub 22 is configured to receive one or more interventional tools and is coupled to curvable portion 16 by a junction 28. Junction 28 may be coupled to a clasp 30 at a junction 32. In one or more implementations, junction 28 may comprise a medical grade material or the like. For instance, junction 28 may be manufactured from a medical grade plastic or the like. Moreover, junction 28 is configured to stabilize curvable portion 16. Junction 32 provides connective functionality to clasp 30. For example, clasp 30 may couple to junction 32, which allows clasp 30 to couple to junction 28. While FIGS. 1A, 2, and 5 illustrate clasp 30 coupled to notch 34, clasp 30 may be configured to be selectively coupled to shunt 12, detachable member 18, or the like. When coupled to notch 34, or the like, clasp 30 holds the device in a position such that septum hub 22 is oriented in a direction opposite from that of shunt 12 or a variation of this direction. When the clasp 30 is disengaged from shunt 12, the flexible nature of curvable portion 16 allows septum hub 22 to be arranged generally in-line with shunt 12. In another implementation, septum hub 22 may be arranged in a variety of positions and at angles between 0° (i.e. in-line) and 180° (or possibly more if required) relative to shunt 12. In yet another implementation, septum hub 22 may be exchanged with other hub adaptors (not shown) depending on operator/technician, plumbing position, and interventional needs. Moreover, in an implementation, the detachability and interchangeability of sheath 10 components may allow increased stiffness of the detachable curvable, external portion 16.

While sheath 10 is shown as a complete sheath, sheath 10 could be used in conjunction with existing sheaths and sheath components. As described above, sheath 10 may also be comprised of separate, detachable components at detachable member 18. In such implementations, sheath 10 could be used with existing components that allow for curvatures internal to the patient. For example, the internal, distal, and proximal, curved components of sheath 10 can be interchanged with currently available sheaths if the locking systems match. In addition, existing sheath components may be used with portions of sheath 10 to provide a sheath that may be selectively configured to provide a 180° curve. In such embodiments, curvable portion 16, detachable member 18, junction 28, and clasp 30 may be provided as a single unit that would be used to retrofit an existing sheath design.

In selecting sheathing for curvable portion 16, consideration for the largest internal diameter with a solid, kink resistant material is given. For example, curvable portion 16 may be comprised of a nitinol wire impregnated plastic sheath. Both coiled and cell design impregnated sheaths may be useful, though coil designs are likely preferable to maintain flexibility. Conventional portions of sheath may be manufactured from materials normally used for such items. When attachable/detachable components are utilized, stiffness of components may increase.

The sheath 10 should also have an acute change in caliber at the proximal portion of shunt 12, limiting sheath migration, as well as having a notch 34 within this diameter enlargement. The notch 34 may act as an attachment for a clasp 30, locking the two parallel ends of the sheath 10. The clasp 30 will allow stability of sheath 10 and will counter against the movements of interventional tools within the sheath 10 and internal vasculature.

As illustrated in FIGS. 1A and 2 through 4, clasp 30 is shown extending from junction 28 where it is coupled at junction 32. Clasp 30 comprises a shank portion 40 and a clasping portion 42. In an implementation, the clasping portion 42 may have a generally arcuate configuration or the like. Clasping portion 42 extends at least partially about detachable member 18 and may engage notch 34 to secure sheath 10 in a "closed" (i.e., curved) configuration. In this sense, the "closed" configuration is one in which septum hub 22 is oriented in a direction generally opposed to the direction of shunt 12 and clasp 30 engages detachable member 18. Moreover, when the sheath 10 is in the "closed" configuration, first end 44 of the curvable portion 16 is proximate to second end 46 of the curvable portion 16. This configuration allows an operator or technician to access a vascular conduit through sheath 10, and, in those situations where the vascular conduit may be accessed from a position proximate to the patient's torso, head, or abdomen, the operator may be positioned away from those parts of the patient.

Figure 3:
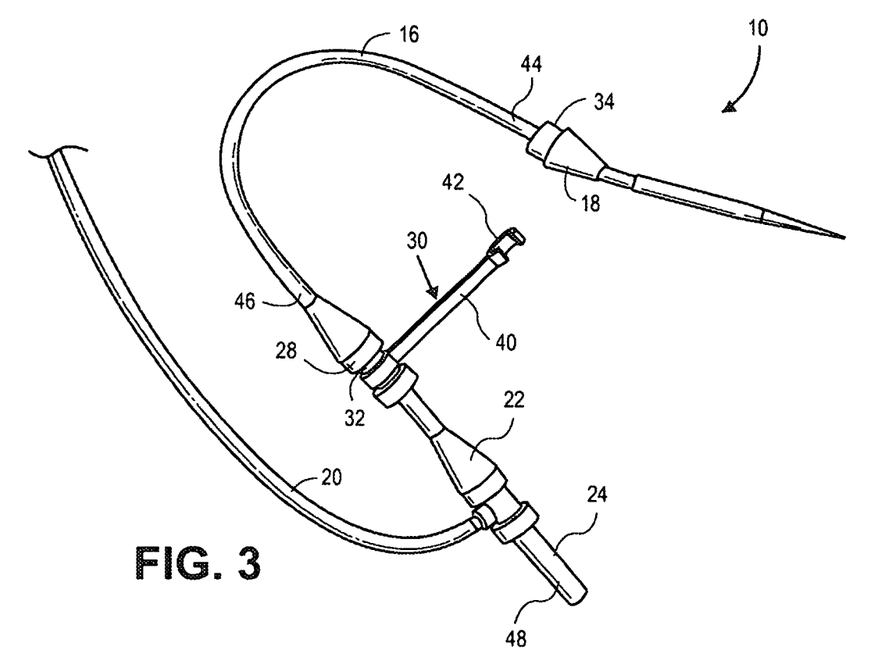
FIG. 3 is a diagrammatic isometric view illustrating the sheath depicted in FIG. 1A, where the sheath is in an open (i.e., unclasped) position.
Figure 4:
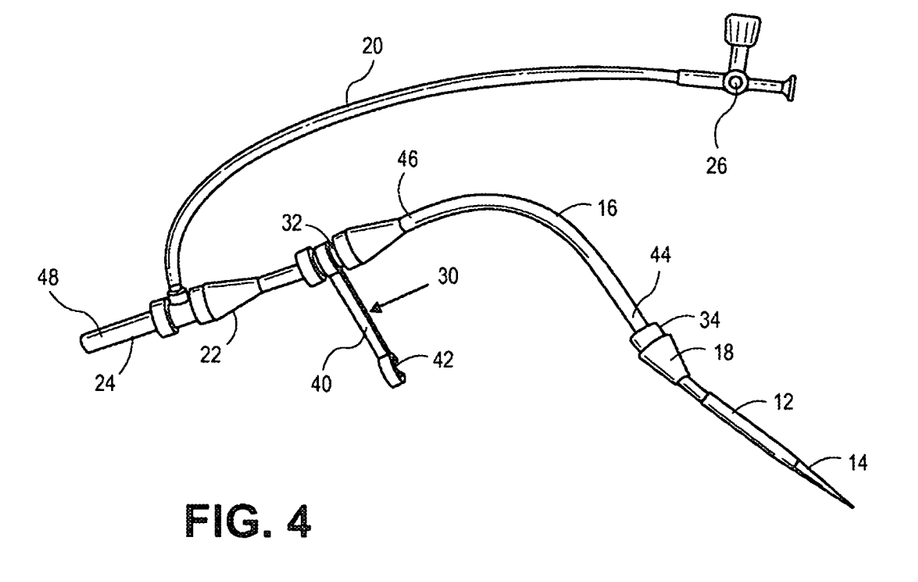
FIG. 4 is another diagrammatic isometric view illustrating the sheath depicted in FIG. 3, where the sheath is in an open (i.e., unclasped) position.

Referring to FIGS. 3 and 4, sheath 10 is in an "open" position where clasp 30 is disengaged from detachable member 18. While it is shown that the "open" position may be semi-curved, it is understood that the curvable portion 16 may retain a substantially straight configuration. For example, the curvable portion 16 may be positioned by an operator so that the curvable portion 16 retains a substantially straight configuration. In the substantially straight configuration, the first end 44 may be linearly distal to the second end 46. Moreover, member 48 of sheath 10 proximate to septum hub 22 may be more freely manipulated by an operator or technician due to the flexibility of curvable portion 16. For example, sheath 10 may be used in a position that places the flow at septum hub 22 perpendicular to that of shunt 12 (as illustrated in FIG. 4), which allows the operator or technician to utilize an angiography machine to visualize vascular structures in the patient while the operator or technician remains outside the radiation field produced by the angiography machine. The sheath 10 may eliminate or reduce possible exposure of the operator or technician to radiation, while allowing for the simultaneous use of tools that may be inserted through septum hub 22 to access the vascular conduit within the patient.

FIGS. 5 through 9 illustrate one or more sheath(s) 10 utilized in a medical environment. For example, the sheath 10 disclosed herein may be readily useable in hemodialysis intervention. Other potential uses include antegrade percutaneous arterial intervention of the common femoral artery, or similar accessible vessel, whereby an operator can work along side of extremity without working near a patient's abdomen, chest, and head. Moreover, the sheath 10 may also be useful for treatment of renal collecting system intervention. The sheath 10 also has potential for patients with ureteral strictures, status post cystectomy, and in urinary conduit formation. Moreover, sheath 10 may be utilized in conjunction with the treatment of the biliary tree, portal venous system, gastrointesintal tract, and spinal canal/thecal sac.

Additional uses for the sheath 10 may be realized with the addition of exhalable or detachable appendages. For example, a larger curvable portion 16 may be used for larger patients receiving lower extremity intervention. Other adaptations include the use of a Toughey-Borst fitting to allow the simultaneous introduction of a fluid while using a guide wire during catheterization. A double lumen or bifurcated sheath may be used for therapy requiring two wires and access sites, from one approach. A larger internal diameter may be used to create larger communication for a suction thrombectomy.

In some embodiments, a kit may comprise a single sterile prepackaged assortment of sheath components. Such kits may include a plurality of curvable portions 16 being of different lengths and/or diameters to allow for the physician to customize the sheath 10 for a particular patient or procedure. For example, a longer curvable portion 16 may be used to facilitate antegrade access to the femoral artery for peripheral vascular disease treatment of the ipsilateral extremity, and give the physician the ability to position him/herself in the area of the patient's legs rather than by the patient's abdomen. The longer curvable portion 16 may be curved around the patient's leg and towards the feet to provide the physician and patient with greater comfort during a procedure.

In some implementations, a kit may include a portion of sheath configured to provide an arcuate portion (similar to curvable portion 16) with conventional couplers. The kit would allow for the modification of existing sheaths to an adjustable sheath with the ability to provide a bend of about 180°. For example, the arcuate portion may be configured to couple to an inductor (not shown) of an existing sheath (not shown). Moreover, the kit would allow an interventionist to modify a sheath system after placement in the patient if it is decided that a curved sheath would be advantageous.

While sheath 10 is in use, the physician or other operator may exert force to advance a catheter, needle, guide wire, or other device through the sheath 10. When the sheath 10 is arranged into a 180° curve, this force acts to pull the sheath out of the patient at the access point. Accordingly, it would be advantageous to provide a stabilizing means for sheath 10 while in use. Such a means may include an adhesive patch (not shown) for securing the sheath to the patient at a point proximate to the access point. Such patches include the STAT-LOCK available from C.R. BARD INC. of Murray Hill, N.J. Other stabilization devices may include external devices such as stabilizing boards that are coupled to the patient and sheath 10 by straps, clasps or other conventional coupling means. Sheath 10 may also be provided with a stabilizing portion that includes apertures for the placement of sutures to secure sheath 10 to the patient.

Figure 10:
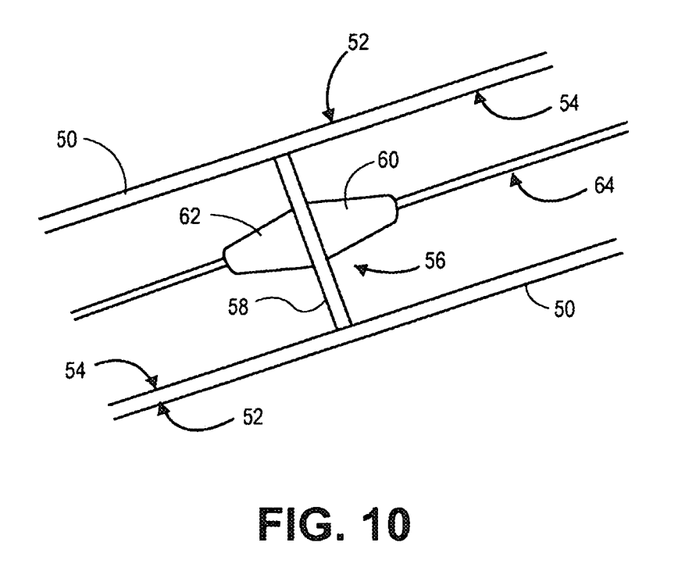
FIG. 10 is a longitudinal cross-sectional view of an anti-backflow exchange wire utilized to prevent fluid/blood backflow when exchanging various detachable components associated with the sheath depicted in FIG. 1.
Figure 11:
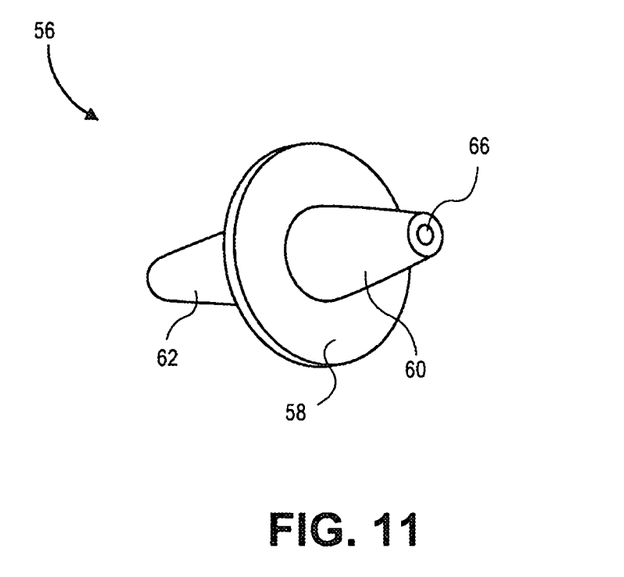
FIG. 11 is a perspective view of the septum of FIG. 10.

Sheath 10 may further include an anti-backflow exchange wire, which is illustrated in FIGS. 10 and 11. The anti-backflow exchange wire is configured to block backflow that may occur when an operator/technician removes back end components of sheath 10. Thus, an operator/technician may interchange the sheath's 10 back end components (e.g. converting from a straight, short 5 cm sheath, to a 180 degree curved, tennis racket shaped sheath, and so forth) with minimal to no leakage when utilizing the anti-backflow exchange wire. A septum (e.g., a valve or seal) may attach to the wire (such as a 0.018 inch or a 0.035 inch wire) and configured to block flow within the sheath 10. The septum may be configured to move within sheath 10 while maintaining a seal against the interior wall of sheath 10. The septum may be fixed in relation to the wire. In use the septum moves with the wire as it is advanced through the sheath and prevent the backflow of blood or other fluids. When the wire is retracted, the septum moves with the wire. This can be done to allow completion of a procedure while minimizing the release of fluids through sheath 10 out of the patient that could obscure the view of the operator or cause couplings to become stuck. Moreover, sheath 10 may be used with a variety of catheterization devices including guide wires.

Referring to FIGS. 10 and 11, sheath section 50 has an exterior wall 52 and an interior wall 54. Septum 56 is sized to seal the interior diameter of sheath section 50 while allowing septum 56 to slide relative to interior wall 54. Septum 56 includes a disc portion 58 and two lugs 60 and 62. Lugs 60 and 62 may be provided with a longitudinal aperture 66 for receiving wire 64. Disc 58 may have an aperture coaxial with aperture 66. Disc 58 may also be punctured when wire 64 is passed through the aperture 60 through lugs 60 and 62. Lugs 60 and 62 may be separate parts from disc 58. Lugs 60, 62, and disc 58 may also be formed as a single unitary body to provide septum 56. Wire 64 may be passed through septum 58 prior to placing septum 56 in sheath section 50. The friction between wire 64 and septum 56 may be sufficiently greater than the friction between septum 56 and interior wall 54 such that once septum 56 is placed in sheath section 50, the force required to move septum 56 relative to interior wall 54 is greater than the force required to move wire 64 relative to septum 56. Lugs 60 and 62 with passage 66 provide a greatly increased surface area over which septum 56 contacts wire 64 compared to the contact area provided by disc 58. Such a configuration allows septum 56 to move within sheath section 50 while remaining static with respect to wire 64 and maintaining a seal against the backflow of fluids.

Conclusion

Although a few exemplary embodiments of the present invention have been shown and described, the present disclosure is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A method of using a sheath device, the method comprising:
   positioning a detachable shunt member through a perforation in a side wall of an anatomical vessel, the detachable shunt member including:
   a distal opening configured to reside in the anatomical vessel, and a connection member that resides external to the anatomical vessel and that includes a first septum configured to receive an interventional tool therethrough;
   mating a detachable curvable sheath tube to the connection member including the first septum of the shunt member, wherein the detachable curvable sheath tube includes: a distal end that is smaller in outer diameter than, and detachably mated with, a proximal end of the connection member of the shunt member such that the distal opening of the shunt member remains distal of the distal end of the detachable curvable sheath tube; and a proximal end opposite from the distal end, and a tube wall configured to bend between a curved configuration and a substantially straight configuration, wherein the proximal end of the detachable curvable sheath tube is coupled with a septum hub configured to receive the interventional tool, the septum hub having an introducer portion at a proximal end of the septum hub and a secondary tube for injecting or suctioning fluids;
   moving the interventional tool within an internal access path through the septum hub, the detachable curvable sheath tube, the shunt member, and the anatomical vessel while the distal end of the detachable curvable sheath tube remains fixed relative to the proximal end of the connection member.

2. The method of claim 1, wherein the detachable curvable sheath tube has a longitudinal length extending between the distal end and the proximal end that is greater than the maximum longitudinal length of the shunt member.

3. The method of claim 2, wherein the tube wall of the detachable curvable sheath tube has a maximum outer diameter that is less than the maximum exterior diameter of the shunt member.

4. The method of claim 2, further comprising visualizing vascular structures using a radiation field on a patient in which the shunt member is positioned, wherein the longitudinal length of the detachable curvable sheath tube is sufficient to maintain a user of the septum hub outside of the radiation field.

5. The method of claim 4, wherein the radiation field is produced by an angiography machine.

6. The method of claim 1, further comprising arranging the tube wall of the detachable curvable sheath tube in the curved configuration such that the anatomic vessel is accessed by the shunt member from a position proximate to a head, torso, or abdomen while a user of the interventional tool is positioned away from said head, torso, or abdomen.

7. The method of claim 1, wherein the detachable curvable sheath tube forms a 180° curve when the tube wall of the detachable curvable sheath tube is in the curved configuration.

8. The method of claim 1, wherein the tube wall of the detachable curvable sheath tube comprises a plastic sheath impregnated with a metal wire coil or cell structure.

9. The method of claim 1, wherein the tube wall of the detachable curvable sheath tube comprises nitinol wire impregnated plastic sheath.

10. The method of claim 1, further comprising using a dilator that extends from the distal opening of the shunt member.

11. The method of claim 1, further comprising injecting any of contrast, fluids, and medications through the secondary tube of the septum hub.

12. The method of claim 11, wherein a proximal end of the secondary tube is positioned away from the septum hub and includes a 3-way stop cock valve device.

13. The method of claim 1, further comprising suctioning a fluid through the secondary tube of the septum hub.

14. The method of claim 1, wherein the septum hub is coupled with the proximal end of the detachable curvable sheath tube by a junction.

15. The method of claim 14, further comprising retaining the detachable curvable sheath tube in the curved configuration using a clasp device secured between the junction and the shunt member.

16. The method of claim 1, wherein the shunt member is about 5 centimeters in length.

* * * * *